United States Patent [19]

Hollinger

[11] Patent Number: 5,011,495

[45] Date of Patent: Apr. 30, 1991

[54] UNIQUE BONE REGENERATION TRICALCIUM PHOSPHATE

[75] Inventor: Jeffrey O. Hollinger, Glenwood, Md.

[73] Assignee: The United States of America as represented by the Secretary of the Army, Washington, D.C.

[21] Appl. No.: 481,094

[22] Filed: Feb. 16, 1990

[51] Int. Cl.$^5$ .............................................. A61F 2/28
[52] U.S. Cl. ..................................................... 623/16
[58] Field of Search ..................................... 623/16–23

[56] References Cited

U.S. PATENT DOCUMENTS

| | | | |
|---|---|---|---|
| 4,322,398 | 3/1982 | Reiner et al. | 623/16 |
| 4,497,075 | 2/1985 | Niwai et al. | 623/16 |
| 4,629,464 | 12/1986 | Takata et al. | 623/16 |
| 4,654,314 | 3/1987 | Takagi et al. | 623/16 |
| 4,693,986 | 9/1987 | Vit et al. | 623/16 |
| 4,780,450 | 10/1988 | Sauk et al. | 623/16 |

*Primary Examiner*—David J. Isabella
*Attorney, Agent, or Firm*—Werten F. W. Bellamy; Anthony T. Lane

[57] ABSTRACT

Although many materials have been used for osseous wound repair, no agent currently available provides the surgeon with a predictable level of bone regeneration. Because they do not elicit elicit immunologic responses, and because of the disadvantages of obtaining donor bone, ceramic compositions such as phosphate-bonded alumina and similar ceramics have been investigated as possible bone substitutes capable of promoting bone growth. Since ceramic tricalcium phosphate is biodegradable it has been the subject of considerable research. Despite the research effort, the use of tricalcium phosphate ceramic materials in the regeneration of bone is still subject to improvement. A distinctive form of ceramic beta tricalcium phosphate, modified to augment bone regeneration is provided herein. It is readily implantable in a bone cavity to promote formation throughout the cavity of new bone to replace that lost through trauma, disease, respective surgery, and birth defects.

3 Claims, No Drawings

UNIQUE BONE REGENERATION TRICALCIUM PHOSPHATE

BACKGROUND OF THE INVENTION

This invention relates to the restoration or regeneration of bone lost through trauma, disease, resective surgery, and birth defects. In a more specific aspect the invention is concerned with materials capable of promoting bone growth.

Although many materials have been used for osseous wound repair, no agent currently available provides the surgeon with a predictable level of bone regeneration. Autogenous grafts and allogeneic implants are substances commonly used by surgeons to treat bone defects, and these are the result of considerable research to find an ideal material for restoration of bone. Thus, it has been known for years that bone matrix elicits a type of morphogenetic response. Because of this regeneration inducing capacity, demineralized bone matrix (DBM) has been used for repair of congenital and injury produced bone defects. However, in pediatric skeletal deficiencies, and in adults with loss of extensive amounts of bone, the individual cannot provide sufficient donor bone. In addition immunological limitations are a consideration in the use of DBM. Accordingly, other osteogenic approaches have been pursued. Such approaches include Marshall Urist's bone morphogenetic protein (BMP), and my antigen extracted, autolysed, xenogeneic (AAX) bone, which is the subject of copending application Ser. No. 447,345, filed Dec. 7, 1989.

Because they do not elicit immunologic responses, and because of the disadvantages of obtaining donor bone, ceramic compositions such as phosphate-bonded alumina and similar ceramics have been investigated as possible bone substitutes. Ceramic implants have high compressive strength; they do not degrade; they allow actual attachment of fibrous connective tissue and muscle; and they have specific gravities, coefficients of friction, strength, and surface qualities which are very similar to bone. It has been found that when ceramics are implanted, connective tissue proliferates in the pores, and trabeculae of bone are deposited on and throughout the porous structure. In addition they do not elicit an immunologic response Whereas biodegradable and nonbiodegradable ceramic materials have been shown to offer promise as bone substitutes, biodegradable ceramics are preferred so that no surgical procedure is required to remove the ceramic. Since ceramic tricalcium phosphate is biodegradable it has been the subject of considerable research, as can be learned by referring to U.S. Pat. Nos. 4,781,183, 4,772,468, 4,610,692, 4,599,085 and 4,202,055, as well as *The Journal of Orthopedic Research*, Vol 3, page 301, 1985, and *Proceedings of the 27th Annual Conference on Engineering in Medicine and Biology*, 1974, Volume 16, published by The Alliance for Engineering in Medicine and Biology.

It has been found that despite the research effort the use of tricalcium phosphate ceramic materials in the regeneration of bone is still subject to improvement. The invention herein provides a distinctive form of ceramic beta tricalcium phosphate, modified to augment bone regeneration, the improvement having been reported in the *Journal of Biomedical Materials Research*, Vol 23, pages 17-19 (1989).

SUMMARY OF THE INVENTION

This invention provides a unique form of tricalcium phosphate which maximizes bone regeneration. Its combination of formed pores and density enhances directed bone growth throughout the tricalcium phosphate. A biodegradable pharmaceutical composition is thus provided which is readily implantable in a bone cavity to promote formation throughout the cavity of new bone to replace that lost through trauma, disease, resective surgery, and birth defects. The composition is a tricalcium phosphate ceramic which is only partially densified thereby modifying its physical characteristics, improving its properties over those of prior art ceramic tricalcium phosphates to enhance osteoconduction and osteoinduction. These improved physical properties confer on the resulting implant the capacity for regenerating bone more rapidly than other tricalcium phosphate ceramics.

In addition the tricalcium phosphate (TCP) composition of this invention is fabricated in the form of a stratified tricalcium phosphate disc capable of being shaped to fit the cavity. Disc strata are layers of porous tricalcium phosphate. Each layer has its own distribution of randomly occurring pores, the majority of which are in the size range of 70 to 420 microns. In addition the disc has a density leading to more rapid biodegradation. The harmonious biodegradation and bone ingrowth results in the reconstitution of lost bone by new physiologically responsive bone.

DETAILED DESCRIPTION OF THE INVENTION

Calcium phosphate ceramics are well known as can be seen by referring to the prior art. The calcium phosphate can be tricalcium phosphate, or calcium orthophosphates such as secondary calcium phosphate (dicalcium hydrogenphosphate) or tertiary calcium phosphate (tricalcium phosphate), and even more complex forms of calcium phosphate such as hydroxyapatite. Other forms include tetra calcium phosphate and even octa calcium phosphate. The most used form of calcium phosphate is beta tricalcium phosphate which is substantially pure, having been formed by high temperature calcination of tricalcium phosphate powder. The unique features of this invention are not so much in the form of the calcium phosphate as in its structure.

It has been discerned that new regenerating bone from skeletal margins surrounding a ceramic implant grows into the pores of the ceramic in centripetal fashion. It has been learned that if TCP degrades too rapidly fibrous union takes place across the opening without osseous repair. Moreover, if there are too few pores in the ceramic TCP osseous is extremely slow. We have found that if the TCP is sintered to less than theoretical these shortcomings are avoided. If the TCP is sintered to at least 65 per cent theoretical density rapid degradation is avoided. In addition, if the TCP is sintered to up to 90 per cent theoretical density in forming the ceramic, sufficient porosity remains for rapid bone regeneration. Further, pore orientation is important. To this end we form laminated discs from extrusions. These laminated discs are then calcined to the preferred density less than theoretical, but in the range of 65 to 90 per cent theoretical.

The following example shows how this structure is obtained.

EXAMPLE 1

PREPARATION OF OTCP DISCS

The tricalcium phosphate was prepared from calcium carbonate and phosphoric acid by slowly mixing these two components at 180° F. Following 12 hours of drying under vacuum at 220° F. to produce a powder, the product was analyzed by X-ray analysis. This analysis revealed the product to be hydroxyapatite with a trace of monolite. The powder surface area was 13.6m$^2$/gm. After analysis, the material was dry ball milled for 2 hours in a polyethylene container using aluminum oxide balls. The powder so developed was calcined for 3 and ½ hours at 1500° F. To break up sintered agglomerates, the calcined powder was again ball milled, now with hexane, for 12 hours in a polyethylene jar with aluminum oxide balls. To manufacture the omnidirectional tricalcium phosphate (OTCP) discs, the recognized naphthalene void technique was used. The resulting critical powder volume concentration equaled 64.0% with the binder concentration being 14 weight % organic and 86 weight % beta tricalcium phosphate. The organic binder then had to be removed from the TCP. This was accomplished by a 10 day burnout cycle with a heating rate of 2° F. per hour. To form the desired TCP discs for implantation, sheets of the beta tricalcium phosphate (TCP) were formed by the known hot extrusion methodology using a special die purchased from Braebender Plastograph Company to accomplish the laminating and rolling to produce TCP in the form of 25 mm by 1.5 mm sheets. The discs were then formed by heat-laminating the sheets in alternating layers disposed ninety degrees from each other. After burnout, the matrix produced was heated 1 hour to 2000° F. and held for 2 hours, producing a final disc structure with a sintered matrix density of 82% of theoretical.

The resulting disc had non-interconnected pores, the majority of which were in the range of 70 to 420 microns, randomly arranged throughout the disc. Pore configuration often resulted in many blind alleys. The disc configuration consisted of sintered 100% beta phase TCP, determined by x-ray diffraction spectra. The three layers that had been embossed as a single, three tiered, structure had a final dimension that was a disc of 15 mm×3 mm.

EXAMPLE 2

TEST RESULTS

Materials

To illustrate the effects of discs of this invention on bone growth, the OTCP ceramic discs of Example 1 were compared with unidirectional tricalcium phosphate (UTCP) ceramic discs having very few small pores in the 100 to 150 micron range, simulating TCP sintered to theoretical. In view of the small pores, to prevent mechanical hooking, and to permit ingress of host osteogenic and mesenchymal cells, each disc layer was provided with microchannels. To form these microchannels the sheets were embossed and laser drilled with a Neodymium glass pulse laser to produce 600 micron channels passing therethrough. Microchannels in each of the three adjacent layers were disposed in different directions so that new regenerating bone would grow in all directions through the microchannels, but the final TCP disc had its pores all in one direction (omnidirectional).

Procedure

Implants were steam sterilized prior to insertion into the experimental animals. Sixty adult New Zealand white rabbits (skeletal maturity determined by radiographic closure of epiphyseal plates) of mixed sex, weighing 6-7 lbs. were divided equally into 3 treatment groups: UTCP, OTCP and control. The anesthetic was a cocktail of ketamine HCl, USP (100 mg/mL), xylazine, USP (100 mg/mL), and sterile water (10:1:5, by volume) administered intramuscularly at a dose of 1 cc/4 lbs. into the left hind leg. Prophylactic antibiotic coverage was obtained by using 300,000 units if benzathene penicillin G and procain penicillin G (Flocillin ®)) in the right hind leg 1 h before surgery. Calvarias were prepped, draped, and an incision was made in the midsagittal line of the skull. The skin and periosteum were reflected and a 15-mm craniotomy was created in the parietal bones, using a trephine in a dental rotary handpiece with copious sterile saline irrigation. Circular UTCP or OTCP implants of identical size to the craniotomies were inserted securely into the bony wounds (FIGS. 1f,g) and soft tissue was closed in layers with 3-0 Dexon sutures. Each of the three treatment groups was divided equally into four temporal groups of 12, 24, 36, and 48 weeks. At the appropriate time, each group was euthanatized with an overdose of sodium pentabarbital. The calvarias were exposed and the implant and control sites were removed with approximately 2-3 mm of surrounding host bone using a number 703 dental bur and copious saline irrigation.

The percentage of remaining UTCP and OTCP across the 15-mm craniotomies and the area of bony fill in the three treatment groups were determined by random measurements of six fields from bony margin to bony margin. Between group comparisons of the remaining TCP and area of osseous fill at each time period were made using a Student's t-test for unpaired data. The results are given in the following tables.

TABLE I

| | Mean Area of Bone Fill (mm$^2$) | | |
|---|---|---|---|
| Treatment time (weeks) | OTCP (±SD) | UTCP (±SD) | Control (±SD) |
| 12 | 2 ± 0.5 | 4 ± 1.0 | 5 ± 2.0 |
| 24 | 18 ± 3 | 13 ± 2 | 18 ± 4 |
| 36 | 82 ± 6 | 21 ± 2 | 23 ± 3 |
| 48 | 123 ± 11 | 29 ± 5 | 49 ± 6 |

TABLE II

| | Mean Percentage Remaining TCP | |
|---|---|---|
| Time (weeks) | OTCP (±SD) | UTCP (±SD) |
| 12 | 89 ± 6 | 91 ± 5 |
| 24 | 78 ± 5 | 84 ± 6 |
| 36 | 43 ± 3 | 80 ± 7 |
| 48 | 9 ± 1 | 78 ± 5 |

OTCP = omnidirectional tricalcium phosphate
UTCP = unidirectional tricalcium phosphate
SD = standard deviation The data in Tables I and II clearly demonstrate the merits of this invention. After 48 weeks the mean percentage of remaining TCP to be replaced by bone in the case of OTCP was about 9 per cent. When UTCP was employed, about 78 per cent TCP remained to be replaced by bone after 48 weeks. Referring to Table I, an area of the cavity of about 123 mm$^2$ was filled with bone when OTCP was employed, whereas using UTCP, an area of only about 29 mm² of the cavity was filled. Clinical findings revealed virtually no changes at the OTCP or UTCP periphery. Controls, on the other hand, displayed fibrous union across the 15-mm craniotomy with very little evidence of bone repair. Implants appeared tissue-tolerant. At 12 weeks both configurations of implants were similar in appearance. Histologically and histomorphometrically, by 48 weeks approximately 90 per cent of the OTCP implant discs had degraded, and the OTCP was replaced with woven bone and maturing lamellar bone. Radiographically, the impression was similar to the clinical and histological findings. At the end of the 48 weeks both implantations were hard and firmly fixed to the host margins without any indication of adverse tissue reaction. There was a suggestion of more peripheral decay of material in the OTCP than in the UTCP. However, centrally there was some evidence of OTCP.

It can be seen that this invention provides a tricalcium phosphate implant disc capable of promoting bone growth which is unlike any of the prior art TCP implant materials. It will be appreciated too that, as an important aspect of this invention, microchannels such as those described in Example 2 can be formed in the TCP discs of the invention. To further improve the disc implants, they can be fabricated with microchannels in the 450 to 700 micron size range, preferably 600 micron ducts.

Having been given the teachings of this invention variations and ramifications will occur to those skilled in the art. Thus the TCP can be employed in combination with bone growth factors. Growth factors are known protein and polypeptide materials, such as platelet-derived growth factors, insulin-like growth factors, epidermal growth factors, and transforming growth factor beta. In addition the TCP of the invention can be prepared in combination with a bone inductive protein such as BMP, xenogeneic bone such as AAX, and with calcification initiators such as D,L-poly(lactide co-glycolide), and polylactic-polyglycolic acids combined with acidic phospholipid-lysozyme complexes. Such modifications are deemed to be within the scope of this invention.

What is claimed is:

1. A biodegradable implant for implanting in a bone cavity comprising a layered disc, each strata are layers of porous tricalcium phosphate; and said disc having a sintered matrix density substantially between 65 and 90% and pores in the range of 70 to 420 microns wherein the pores are omnidirectional for more rapid regeneration of new bone tissue into the disc.

2. The implant of claim 1 further comprising at least one microchannel of a size in the range of 450–700 microns formed in each strata wherein the microchannels of each strata being oriented in different direction.

3. The implant of claim 2 wherein the size of the microchannels is 600 microns.

* * * * *